(12) United States Patent
Yonezawa

(10) Patent No.: US 10,279,151 B2
(45) Date of Patent: May 7, 2019

(54) GUIDE WIRE

(71) Applicant: ASAHI INTECC CO., LTD., Seto-shi, Aichi (JP)

(72) Inventor: Satoshi Yonezawa, Iwate-gun (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 166 days.

(21) Appl. No.: 15/433,514

(22) Filed: Feb. 15, 2017

(65) Prior Publication Data

US 2017/0368316 A1  Dec. 28, 2017

Related U.S. Application Data

(63) Continuation of application No. PCT/JP2016/068922, filed on Jun. 24, 2016.

(51) Int. Cl.
*A61B 5/00* (2006.01)
*A61M 25/09* (2006.01)

(52) U.S. Cl.
CPC ... *A61M 25/09* (2013.01); *A61M 2025/09083* (2013.01); *A61M 2025/09108* (2013.01); *A61M 2025/09133* (2013.01)

(58) Field of Classification Search
CPC ........ A61M 25/09; A61M 2025/09083; A61M 2025/09133; A61M 2025/09175; A61M 2025/09108
See application file for complete search history.

(56) References Cited

U.S. PATENT DOCUMENTS

| | | | |
|---|---|---|---|
| 6,361,626 B1 | 3/2002 | Kitajima et al. | |
| 8,585,613 B2 * | 11/2013 | Nagano | A61M 25/09 600/585 |
| 8,758,269 B2 * | 6/2014 | Miyata | A61M 25/09 600/585 |
| 2011/0319872 A1 | 12/2011 | Kawasaki | |
| 2013/0006221 A1 | 1/2013 | Koike | |
| 2013/0289445 A1 | 10/2013 | Edamatsu | |

FOREIGN PATENT DOCUMENTS

| | | |
|---|---|---|
| JP | 2006-255784 A | 9/2006 |
| JP | 2006-351737 A | 12/2006 |
| JP | 2010-214054 A | 9/2010 |
| JP | 2013-013448 A | 1/2013 |
| JP | 2013-013449 A | 1/2013 |
| JP | 2013-111320 A | 6/2013 |
| JP | 2013-226301 A | 11/2013 |
| JP | 2014-161705 A | 9/2014 |
| JP | 2015-173835 A | 10/2015 |
| WO | 02/034969 A1 | 5/2002 |

OTHER PUBLICATIONS

Jul. 24, 2018 Office Action issued in Japanese Patent Application No. 2016-567099.
Feb. 6, 2018 Office Action issued in Japanese Patent Application No. 2016-567099.

* cited by examiner

*Primary Examiner* — Max F Hindenburg
(74) *Attorney, Agent, or Firm* — Oliff PLC

(57) ABSTRACT

A guide wire including a core shaft, a coil body that covers an outer periphery of the core shaft, and a distal end joint that joins the core shaft and the coil body, The distal end joint includes tin-zinc based solder. The guide wire has secured joining strength between the core shaft and the coil body no matter the material used for the core shaft and the coil body, and especially when the core shaft and/or the coil body are formed of tungsten.

9 Claims, 4 Drawing Sheets

GUIDE WIRE

CROSS REFERENCE TO RELATED APPLICATION

This application is a continuation of PCT/JP2016/068922 filed on Jun. 24, 2016, the contents of which are incorporated by reference herein in their entirety.

BACKGROUND

The disclosed embodiments relate to a medical device. Specifically, the disclosed embodiments relate to a guide wire used for insertion of a catheter into a body lumen such as a blood vessel or a urinary duct, and for insertion of an indwelling instrument into an aneurysm formed in a blood vessel.

The guide wire used for insertion of a catheter into a body lumen and for insertion of an indwelling instrument into an aneurysm generally includes a core shaft, a coil body covering a distal end portion of the core shaft, and a joint joining the core shaft and the coil body.

For example, Japanese Patent Application Laid-open No. 2010-214054 describes a guide wire including a core wire (corresponding to a core shaft) formed of stainless steel, a coil spring (corresponding to a coil body) covering a distal end of the core wire, and a Au—Sn based solder (corresponding to a joint) joining the distal end of the core wire and a distal end of the coil spring (see FIG. 1, etc.). Japanese Patent Application Laid-open No. 2010-214054 also describes that Ag—Sn based solder is conventionally used instead of Au—Sn based solder to join the core wire and the coil spring ((see paragraph [0004], etc.). That is, Japanese Patent Application Laid-open No. 2010-214054 describes that either Ag—Sn based solder (hereinafter referred to as "silver-tin based solder") or Au—Sn based solder (hereinafter referred to as "gold-tin based solder") can be used to join a core shaft formed of stainless steel in the conventional guide wire.

However, the silver-tin based solder and the gold-tin based solder are different in joining strength depending on a material to be joined, and there has been a problem that especially for tungsten, sufficient joining strength cannot be secured for use as a guide wire, as described later.

Moreover, in the guide wire, the joining strength between the core shaft and the coil body is a considerably important element for the performance of the guide wire. For example, when the joining strength between the core shaft and the coil body is insufficient, there is a risk that the core shaft and the coil body will become separated from each other during procedures, and in the worst case, a distal end of the guide wire might remain in a patient's body.

SUMMARY

In view of the above-described problem, the disclosed embodiments aim to provide a guide wire having secured joining strength between a core shaft and a coil body no matter the material of the core shaft or the coil body, and especially when the core shaft and the coil body are formed of tungsten.

In order to achieve this object, a guide wire of the disclosed embodiments includes a core shaft, a coil body that covers an outer periphery of the core shaft, and a joint that joins the core shaft and the coil body. The joint includes tin-zinc based solder. Thus, no matter the material of the core shaft and the coil body, it is possible to sufficiently secure the joining strength between the core shaft and the coil body.

The tin-zinc based solder may include 3.0 to 14.0 wt. % of zinc. For example, the tin-zinc based solder may be formed of 91 wt. % of tin and 9 wt. % of zinc. Thus, the melting point is around 200° C., and the solder can be managed easily. Therefore, no matter the material of the core shaft and the coil body, it is possible to easily secure the joining strength between the core shaft and the coil body.

The coil body and/or the core shaft may be formed of tungsten. Thus, it is possible to secure visibility in irradiation of radiation while sufficiently securing the joining strength between the core shaft and the coil body even when the core shaft and the coil body cannot be joined with silver-tin solder and gold-tin solder. When the coil body is formed of tungsten, it is possible to further secure visibility in irradiation of radiation while sufficiently securing the joining strength between the core shaft and the coil body.

The joint may join the core shaft and the coil body together at their distal ends. That is, the joint may join a distal end of the core shaft and a distal end of the coil body. Thus, it is possible to prevent the core shaft and the coil body from being separated from each other during procedures and thus to prevent a distal end of the guide wire from remaining in a patient's body.

DETAILED DESCRIPTION OF EMBODIMENTS

The following will describe embodiments of the invention with reference to the drawings.

Figure 1:
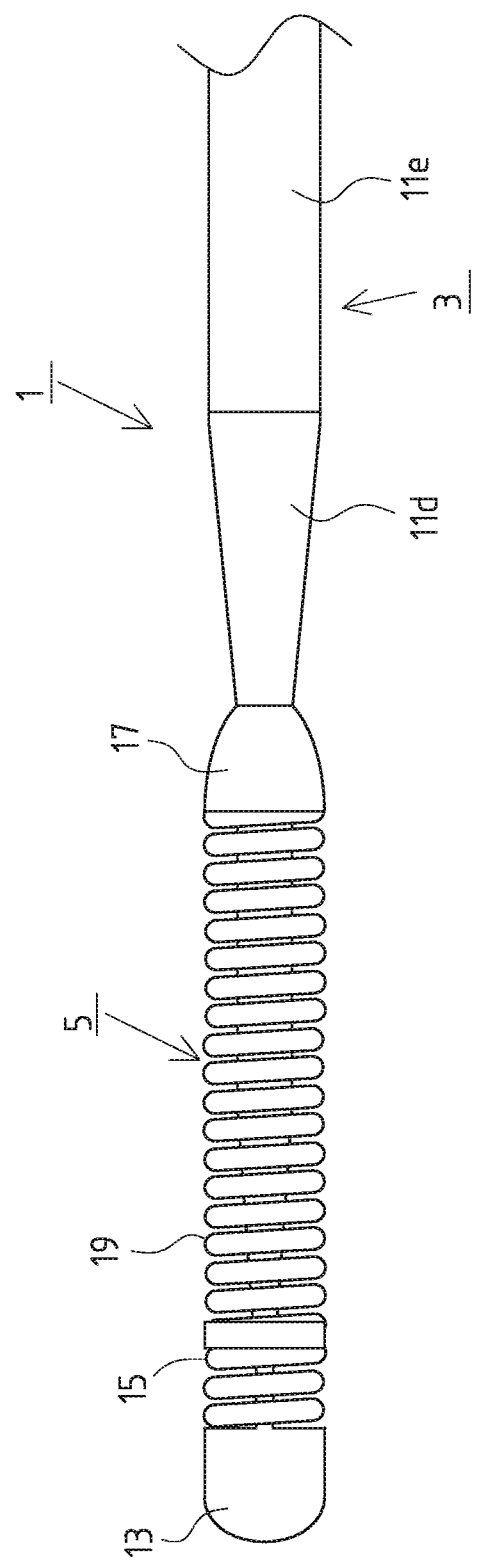
FIG. 1 is a side view of a guide wire according to the disclosed embodiments.
Figure 2:
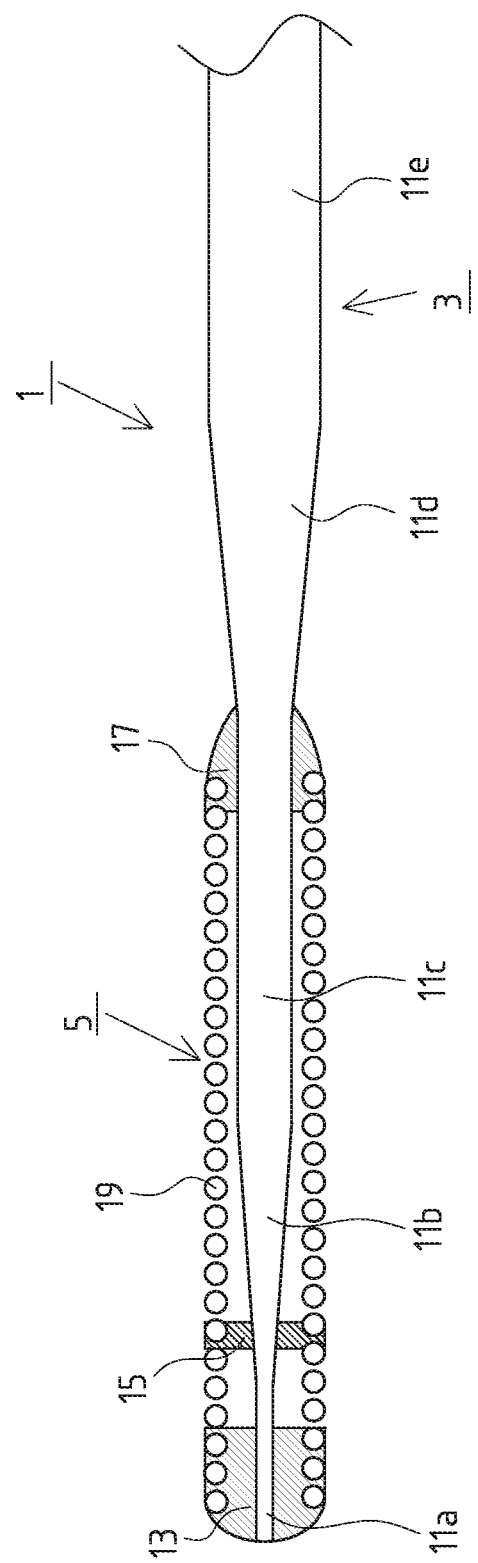
FIG. 2 is a side cross-sectional view of the guide wire shown in FIG. 1.

FIG. 1 is a side view of a guide wire according to the disclosed embodiments. FIG. 2 is a side cross-sectional view of the guide wire shown in FIG. 1.

In FIG. 1, a guide wire 1 includes a core shaft 3, a coil body 5 fixed to a distal end of the core shaft 3, a distal end joint 13 joining a distal end of the coil body 5 and the distal end of the core shaft 3, a proximal end joint 17 joining a proximal end of the coil body 5 and the core shaft 3, and an intermediate joint 15 joining the coil body 5 and the core shaft 3 between the distal end joint 13 and the proximal end joint 17.

The core shaft 3 has a round rod shape tapered from the proximal end toward the distal end, and includes, from the distal end, a cylindrical first distal end portion 11a, a second tapered portion 11b, a third cylindrical portion 11c, a fourth tapered portion 11d, and a fifth cylindrical portion 11e.

Note that as a material of the core shaft 3, tungsten is used, but stainless steel or the like can alternatively be used.

The coil body 5 is formed in a hollow cylindrical shape by helically winding a single piece of metal element wire 19 around the core shaft 3. Note that as a material of the coil body 5, tungsten is used, but stainless steel or the like can alternatively be used.

In the guide wire 1, the coil body 5 is formed in a hollow cylindrical shape by helically winding the single piece of metal element wire 19 around the core shaft 3. However, the coil body 5 may be formed in a hollow cylindrical shape by helically winding a plurality of pieces of metal wire around the core shaft 3, or by helically winding a single piece of stranded wire formed by twisting a plurality of pieces of metal element wire around the core shaft 3, or by helically winding a plurality of pieces of stranded wire formed by twisting a plurality of pieces of metal element wire around the core shaft 3.

The distal end joint 13 forms a distal end of the guide wire 1 with a substantially hemispherical shape, and an outer diameter of a proximal end portion of the distal end joint 13 is substantially the same as an outer diameter of the coil body 5. As a material of the distal end joint 13, tin-zinc based solder (Sn—Zn based solder) can be used. The tin-zinc based solder may include 3.0 to 14.0 wt. % of zinc. In the distal end joint 13, for example, a Sn-9Zn solder with 91 wt. % of tin and 9 wt. % of zinc is used. This material has a melting point of around 200° C. and is relatively easy to manage.

In the proximal end joint 17, an outer diameter of a proximal end portion is substantially the same as the outer diameter of the coil body 5. The material of the proximal end joint 17 may be the same as the material of the distal end joint 13, and tin-zinc based solder (Sn—Zn based solder) can be used. In the proximal end joint 17, for example, Sn-9Zn solder with 91 wt. % of tin and 9 wt. % of zinc is used.

In the intermediate joint 15, the outer diameter is substantially the same as the outer diameter of the coil body 5. The material of the intermediate joint 15 may also be the same as the material of the distal end joint 13 and the proximal end joint 17, and tin-zinc based solder (Sn—Zn based solder) can be used. In the intermediate joint 15, for example, Sn-9Zn solder with 91 wt. % of tin and 9 wt. % of zinc is used.

The guide wire 1 includes the core shaft 3; the coil body 5 covering the outer periphery of the core shaft 3; and the distal end joint 13, the intermediate joint 15, and the proximal end joint 17 that join the core shaft 3 and the coil body 5. The distal end joint 13, the intermediate joint 15, and the proximal end joint 17 include tin-zinc based solder. Thus, no matter the material of the core shaft and the coil body, it is possible to sufficiently secure the joining strength between the core shaft and the coil body.

Moreover, in the guide wire 1, the tin-zinc based solder is formed of 91 wt. % of tin and 9 wt. % of zinc. Thus, the melting point is around 200° C., and the solder can be managed easily. Therefore, no matter the material of the core shaft and the coil body, it is possible to easily secure the joining strength between the core shaft and the coil body.

Moreover, in the guide wire 1, the coil body 5 and the core shaft 3 are formed of tungsten. Thus, it is possible to secure visibility in irradiation of radiation while sufficiently securing the joining strength between the core shaft 3 and the coil body 5 even when they cannot be joined with the conventional silver-tin solder and gold-tin solder.

In the case of considering only visibility in irradiation of radiation during procedures, the coil body 5 and the core shaft 3 are preferably formed of tungsten. However, in the case of considering pushability and torque transmissivity of the whole guide wire in addition to visibility in irradiation of radiation, it is preferable that the core shaft 3 is formed of stainless steel and only the coil body 5 is formed of tungsten.

In the embodiment, tin-zinc based solder is used for the distal end joint 13, the intermediate joint 15, and the proximal end joint 17. In order to prevent the core shaft 3 and the coil body 5 from being separated from each other during procedures (which could result in the distal end of the guide wire 1 remaining in a patient's body), it is only necessary that at least the distal end joint 13 is formed by tin-zinc based solder. In such a case, an adhesive can be used for the intermediate joint 15 and the proximal end joint 17.

The following will describe the test for confirming the joining strength between the core shaft and the coil body that was performed by the applicant.

Figure 3:
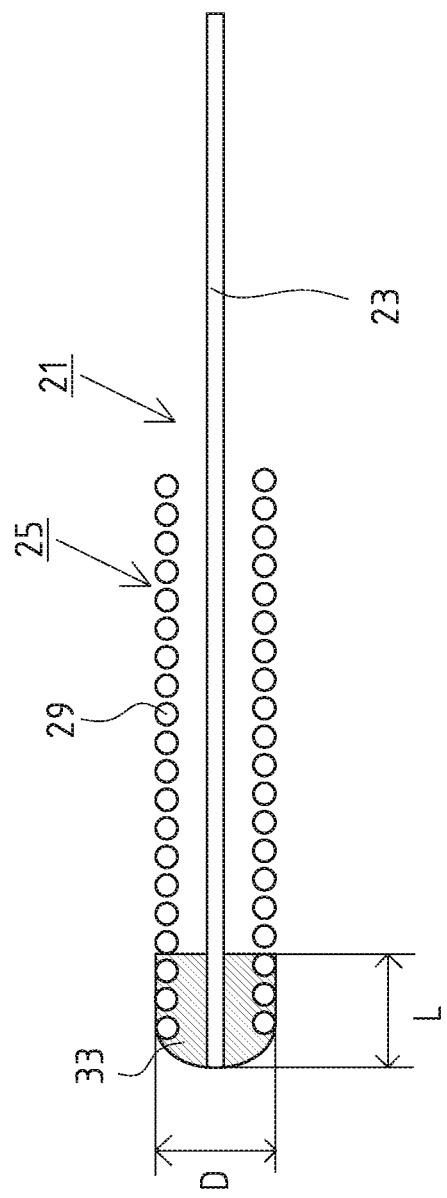
FIG. 3 is a side cross-sectional view of a guide wire used for a joining strength test.
Figure 4:
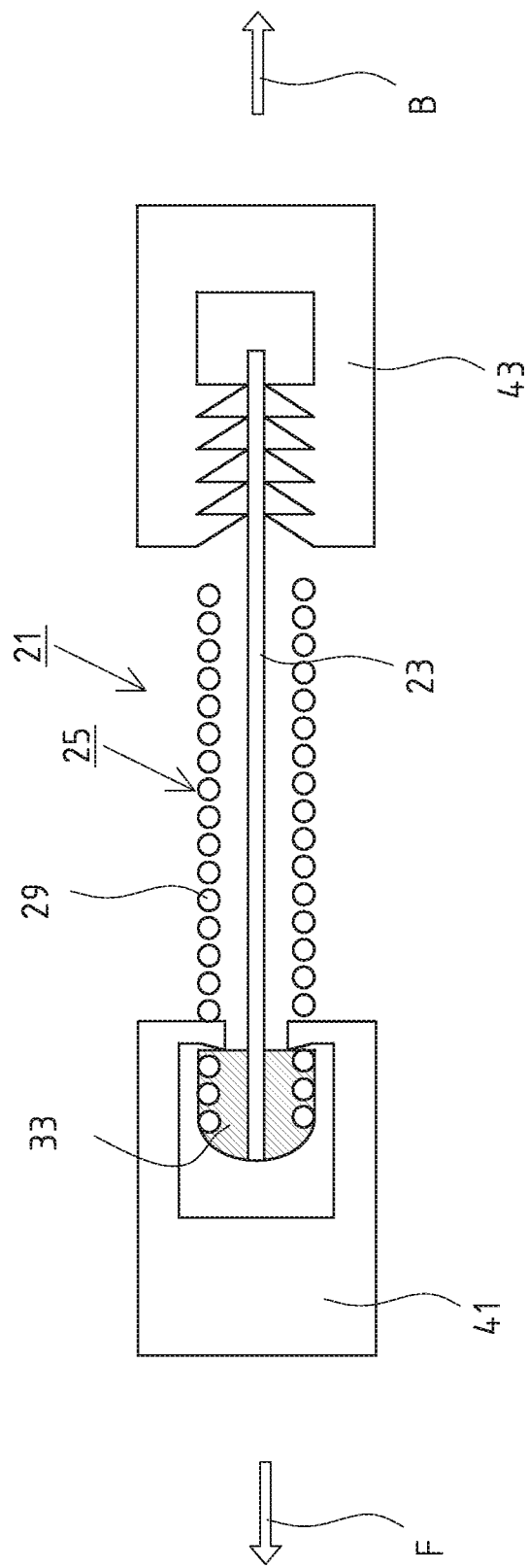
FIG. 4 is an explanatory diagram for explaining the joining strength test.

FIG. 3 is a side cross-sectional view of a guide wire used for the joining strength test. FIG. 4 is an explanatory diagram for explaining the joining strength test.

In FIG. 3, a guide wire 21 used in the test includes a core shaft 23, a coil body 25 that is fixed to a distal end of the core shaft 23 and includes a single piece of metal element wire 29, and a distal end joint 33 joining a distal end of the coil body 25 and the distal end of the core shaft 23. Note that a proximal end of the coil body 25 is not joined to the core shaft 23 for the purpose of measuring the joining strength accurately.

The joining strength test was performed by hanging the distal end joint 33 of the guide wire 21 on a distal end side chuck 41, fixing the proximal end of the core shaft 23 of the guide wire 21 with a proximal end side chuck 43, and then measuring a load when pulling the distal end side chuck 41 in an F direction and the proximal end side chuck 43 in a B direction. The results are shown in Table 1 and Table 2.

Note that the joining strength test conditions are as follows.

(Joining Strength Test Condition 1)

1. Used solder (three kinds)

(1) tin-zinc based solder (Sn-9Zn (tin: 91 wt. %, zinc: 9 wt. %)):

melting point 199° C.

(2) silver-tin based solder (Sn-3.5Ag (tin: 96.5 wt. %, silver: 3.5 wt. %)):

melting point 221° C.

(3) gold-tin based solder (Au-20Sn (gold: 80 wt. %, tin: 20 wt. %)):

melting point 278° C.

2. Used coil element wire (two kinds)

(1) stainless steel (SUS304) coil:

round wire having a cross section with a diameter of 0.08 mm (2) tungsten coil:

round wire having a cross section with a diameter of 0.08 mm

3. Dimension of used coil body outer diameter: 0.42 mm (D: see FIG. 3)

4. Used core shaft stainless steel (SUS304):

round wire having a cross section with a diameter of 0.12 mm

5. Brazing length (L: see FIG. 3)

0.5 mm

6. Number of times of winding the element wire of the coil at a brazing portion 3 to 4 times 7. tensile testing machine MODEL-1305VT/L by Aikoh Engineering Co., Ltd.

TABLE 1

(Joining strength test result 1)

| coil element wire | tin-zinc based solder | silver-tin based solder | gold-tin based solder |
|---|---|---|---|
| stainless steel (SUS304) | 10.59 to 15.40 | 11.21 to 14.45 | 22.81 to 23.49 |
| tungsten | 11.54 to 13.95 | unmeasurable | unmeasurable |

(unit: N)

(Joining Strength Test Condition 2)
1. Used solder (three kinds)
    (1) tin-zinc based solder (Sn-9Zn (tin: 91 wt. %, zinc: 9 wt. %)):
    melting point 199° C.
    (2) silver-tin based solder (Sn-3.5Ag (tin: 96.5 wt. %, silver: 3.5 wt. %)):
    melting point 221° C.
    (3) gold-tin based solder (Au-20Sn (gold: 80 wt. %, tin: 20 wt. %)):
    melting point 278° C.
2. Used coil element wire (two kinds)
    (1) stainless steel (SUS304) coil:
    round wire having a section with a diameter of 0.08 mm
    (2) tungsten coil:
    round wire having a section with a diameter of 0.08 mm
3. Dimension of used coil body
    outer diameter: 0.42 mm (D: see FIG. 3)
4. Used core shaft
    tungsten: round wire having a section with a diameter of 0.12 mm
5. Brazing length (L: see FIG. 3)
    0.5 mm
6. Number of times of winding the element wire of the coil at a brazing portion
    3 to 4 times
7. tensile testing machine
    MODEL-1305VT/L by Aikoh Engineering Co., Ltd.

TABLE 2

(Joining strength test result 2)

| coil element wire | tin-zinc based solder | silver-tin based solder | gold-tin based solder |
|---|---|---|---|
| stainless steel (SUS304) | 11.32 to 14.42 | unmeasurable | unmeasurable |
| tungsten | 11.12 to 13.91 | unmeasurable | unmeasurable |

(unit: N)

The joining strength between the core shaft and the coil body in the guide wire needs to be 3N or higher. In the test results of Table 1 and Table 2, it is confirmed that the tin-zinc based solder used in the disclosed embodiments can be used to join stainless steel and stainless steel, stainless steel and tungsten, and tungsten and tungsten.

By contrast, it is confirmed that the conventional silver-tin based solder and gold-tin based solder can be used to join stainless steel and stainless steel, but cannot be used to join tungsten. That is, in the joining strength test, silver-tin based solder (Sn-3.5Ag (tin: 96.5 wt. %, silver: 3.5 wt. %)) and gold-tin based solder (Au-20Sn (gold: 80 wt. %, tin: 20 wt. %) did not adhere to a tungsten coil, and thus the joining strength could not be measured.

A guide wire according to the disclosed embodiments has been described above. However, the invention is not limited to the above-described embodiments, and can be implemented with various changes without departing from the scope of the invention.

For example, in the guide wire 1, Sn-9Zn solder with 91 wt. % of tin and 9 wt. % of zinc is used as tin-zinc based solder. However, tin-zinc based solder having a zinc content within a range of 3.0 to 14.0 wt. % can join the core shaft and the coil body favorably. Moreover, the tin-zinc based solder can join the core shaft and the coil body favorably when 0.002 to 0.010 wt. % of aluminum (Al) is added in addition to tin and zinc.

What is claimed is:
1. A guide wire comprising:
    a core shaft; and
    a coil body formed of tungsten that covers an outer periphery of the core shaft, wherein:
    a distal end of the core shaft and a distal end the coil body are joined only by a first material, which is formed of a first tin-zinc based solder comprising zinc in a range of from 3.0 to 14.0 wt %, and
    the core shaft and the coil body are joined at a position between the distal end of the coil body and a proximal end of the coil body only by a second material, which is formed of a second tin-zinc based solder comprising zinc in a range of from 3.0 to 14.0 wt %, the second tin-zinc based solder being the same as or different than the first tin-zinc based solder.
2. The guide wire according to claim 1, wherein at least one of the first and second tin-zinc based solders comprises 9 wt % of zinc.
3. The guide wire according to claim 1 wherein at least one of the first and second tin-zinc based solders comprises 91 wt % of tin and 9 wt % of zinc.
4. The guide wire according to claim 1, wherein at least one of the first and second tin-zinc based solders comprises 0.002 to 0.010 wt % of aluminum.
5. The guide wire according to claim 4, wherein the at least one of the first and second tin-zinc based solders comprises 9 wt % of zinc.
6. The guide wire according to claim 1, wherein a third tin-zinc based solder, which is the same as or different than the first and second tin-zinc based solders, joins the core shaft and the proximal end of the coil body.
7. The guide wire according to claim 1, wherein the core shaft is formed of stainless steel.
8. The guide wire according to claim 7, wherein at least one of the first and second tin-zinc based solders comprises 91 wt % of tin and 9 wt % of zinc.
9. A guide wire comprising:
    a core shaft; and
    a coil body formed of tungsten that covers an outer periphery of the core shaft,
    wherein the core shaft and the coil body are joined by a solder consisting essentially of tin and zinc, the solder comprising the zinc in a range of from 3.0 to 14.0 wt %.

* * * * *